(12) United States Patent
Abbosh et al.

(10) Patent No.: US 12,186,065 B2
(45) Date of Patent: Jan. 7, 2025

(54) WEARABLE ANTENNA ASSEMBLY FOR ELECTROMAGNETIC HEAD IMAGING

(71) Applicant: EMvision Medical Devices Ltd, Brisbane (AU)

(72) Inventors: Amin Abbosh, Brisbane (AU); Abdulrahman S. M Alqadami, Brisbane (AU); Nghia Nguyen-Trong, Brisbane (AU); Beadaa Mohammed, Brisbane (AU); Thanh Phong Nguyen, Brisbane (AU)

(73) Assignee: EMVISION MEDICAL DEVICES LTD, Brisbane (AU)

( * ) Notice: Subject to any disclaimer, the term of this patent is extended or adjusted under 35 U.S.C. 154(b) by 816 days.

(21) Appl. No.: 17/273,224

(22) PCT Filed: Sep. 4, 2019

(86) PCT No.: PCT/AU2019/050946
§ 371 (c)(1),
(2) Date: Mar. 3, 2021

(87) PCT Pub. No.: WO2020/047597
PCT Pub. Date: Mar. 12, 2020

(65) Prior Publication Data
US 2021/0353170 A1    Nov. 18, 2021

(30) Foreign Application Priority Data

Sep. 4, 2018 (AU) .................... 2018903275

(51) Int. Cl.
*A61B 5/0507*    (2021.01)
*A61B 5/00*    (2006.01)
(Continued)

(52) U.S. Cl.
CPC .............. *A61B 5/05* (2013.01); *A61B 5/0042* (2013.01); *A61B 5/0507* (2013.01);
(Continued)

(58) Field of Classification Search
CPC ....... A61B 5/05; A61B 5/0507; A61B 5/6803; A61B 5/6814; A61B 5/0042; A61B 5/4064
See application file for complete search history.

(56) References Cited

U.S. PATENT DOCUMENTS

| 2017/0156596 A1 | 6/2017 | Aguilar-Mendoza |
| 2019/0021626 A1 | 1/2019 | Garcia et al. |
| 2019/0320989 A1 | 10/2019 | Verma et al. |

FOREIGN PATENT DOCUMENTS

| WO | 2017/125397 A1 | 7/2017 |
| WO | 2018/098221 A1 | 5/2018 |

OTHER PUBLICATIONS

International Search Report dated Nov. 13, 2019 for International Application No. PCT/AU2019/050946, 6 pages.
(Continued)

*Primary Examiner* — Colin T. Sakamoto
(74) *Attorney, Agent, or Firm* — KNOBBE, MARTENS, OLSON & BEAR, LLP

(57) ABSTRACT

A wearable antenna assembly for tomographic brain imaging of a subject, the antenna assembly including: a resilient cap to be worn on the head of a subject whose brain is to be imaged; an array of antennas at least partially embedded in the cap at respective mutually spaced locations such that, when the cap is worn by the subject, the antennas are arranged around the subject's brain; wherein the cap has a multi-layered structure including a layer composed of graph-
(Continued)

ite and aluminium oxide powders dispersed in PDMS to improve the matching of dielectric properties with those of the subject's head.

16 Claims, 6 Drawing Sheets

(51) Int. Cl.
  *A61B 5/05*    (2021.01)
  *H01Q 1/27*    (2006.01)
  *H01Q 21/06*    (2006.01)
(52) U.S. Cl.
  CPC .......... *A61B 5/4064* (2013.01); *A61B 5/6803* (2013.01); *A61B 5/6814* (2013.01); *H01Q 1/273* (2013.01); *H01Q 21/065* (2013.01); *A61B 2562/046* (2013.01)

(56) References Cited

OTHER PUBLICATIONS

Written Opinion of the International Searching Authority dated Nov. 13, 2019 for International Application No. PCT/AU2019/050946, 8 pages.
Mohd Saiful Riza Bashri, "Wearable Devices for Microwave Head Diagnostic Systems", PhD thesis, The University of Edinburgh, Mar. 2018.
Tanmoy Das et al., "Graphene-based flexible and wearable electronics", Journal of Semiconductors, vol. 39, No. 1, Jan. 2018.
A. S. M. Alqadami et al., "Flexible Quasi-Yagi antenna arrays for wearable electromagnetic head imaging based on polymer technology," 2018 Australian Microwave Symposium (AMS), Feb. 6-7, 2018.
Rod Waterhouse, 'Printed Antennas for Wireless Communications', John Wiley & Sons, 2007, ISBN:9780470510698.
A. S. M. Alqadami et al, "Fabrication and Characterization of Flexible Polymer Iron Oxide Composite Substrate for the Imaging Antennas of Wearable Head Imaging Systems," in IEEE Antennas and Wireless Propagation Letters, vol. 17, No. 8, pp. 1364-1368, May 29, 2018.
S. M. Al-qadami, "Wearable Electromagnetic Head Imaging System for Brain Diagnosis Based on Polymer Technology", PhD Confirmation Seminar, The university of Queensland, Apr. 13, 2018. [retrieved from the internet on Nov. 4, 2019]. <URL: https://www.itee.uq.edu.au/wearable-electromagnetic-head-imaging-system-brain-diagnosis-based-polymer-technology >. +.
Mohd Saiful Riza Bashri: "Wearable Devices for Microwave Head Diagnostic Systems", PHD Thesis, Jan. 1, 2018, pp. ii-xv, 1-168, XP055693183.
Al_Qadami S, M.: "Wearable Electromagnetic Head Imaging System for Brain Diagnosis Based on Polymer Technology", PhD Confirmation Seminar, Apr. 13, 2018, p. 1, XP055792914. Retrieved from the Internet: ectromagnetic-head-imaging-system-brain-diagnosis-based-polymer-technology [retrieved on Apr. 7, 2021].
Abdulrahman S.M. Alqadami et al.: "Fabrication and Characterization of Flexible Polymer Iron Oxide Composite Substrate for the Imaging Antennas of Wearable Head Imaging Systems", IEEE Antennas and Wireless Propagation Letters, vol. 17, No. 8, Aug. 1, 2018, pp. 1364-1368, XP055693185, US ISSN: 1536-1225, DOI: 10.1109/LAWP.2018.2841879 *pp. 1364, right-hand column line 28—p. 1368, left-hand column line 24*.

WEARABLE ANTENNA ASSEMBLY FOR ELECTROMAGNETIC HEAD IMAGING

This application is a U.S. national phase application under 35 U.S.C. § 371 of international patent application No. PCT/AU2019/050946, filed on Sep. 4, 2019, and entitled "WEARABLE ANTENNA ASSEMBLY FOR ELECTROMAGNETIC HEAD IMAGING," which claims priority to Australian patent application No. 2018903275, filed on Sep. 4, 2018.

BACKGROUND

Brain strokes are one of the main causes of disability and death worldwide. According to the Australian Stroke Foundation Organization, in 2017 about 55,831 Australians suffered a life-threatening stroke every nine minutes, and without taking an action this number will increase to one stroke every four minutes by 2050. The time of diagnosis and treatment is critically important for a rapid and complete recovery. Therefore, a fast, portable on-the-spot and accurate detection tool is required to save thousands of lives. Although there are several existing imaging technologies such as x-ray mammography, computerized and positron emission tomography scanning, and magnetic resonance imaging (MRI), these technologies are inaccessible at rural hospitals and in any case are hardly affordable for low-income patients. Most importantly, the large size of such systems makes them almost impossible for a team of paramedics to carry and use on-the-spot for rapid diagnosis. Moreover, these technologies are either based on ionizing radiation or require bulky, static structures that are expensive to use; consequently, it is impractical for these existing tools to be used for ongoing monitoring.

Previous research has demonstrated the feasibility of using low power electromagnetic (EM) waves to detect and diagnose abnormalities within the human brain. This technique has been introduced as a complementary low-cost, fast, and non-ionizing method compared to the standard techniques described above. An EM imaging system consists of a low power antenna array that operates in a low microwave frequency band, and a simple transceiver. Thus, it offers a low-cost, reliable system that can be used as an on-the-spot diagnosis tool.

EM image reconstruction is based on the contrast in the dielectric properties of healthy and unhealthy tissues inside a human head. Since the scattering, penetration and absorbing of an EM signal depends on those properties, differences in those properties can be used to detect abnormalities by reconstructing useful images. Several types of EM head imaging systems have been proposed for brain stroke and cancer detection and diagnosis. However, these systems are not readily available for clinical use due to several difficulties that need to be addressed. The main limitations of existing systems are their size and limited compatibility with the human head, the penetration depth of the electromagnetic signals into the head, antenna mismatch with head tissues, and air-skin interface reflections that cause interference with the useful reflected signals, resulting in inaccurate and low-resolution images.

It is desired, therefore, to overcome or alleviate one or more difficulties of the prior art, or to at least provide a useful alternative.

SUMMARY

The inventors have identified that the imaging antenna array plays a key role in the performance of an EM head imaging system (e.g., image accuracy, detection capability) and its physical characteristics (e.g. portability, flexibility, weight). For an efficient and portable EM head imaging system, a light-weight wearable platform and wideband, low profile, unidirectional, and efficient antenna arrays is required. However, the attainment of an antenna array with such features is highly challenging due to size restraints when operating in the low microwave frequency band, the high mutual coupling between adjacent antennas, and the complexity/high-attenuation of human head tissues that suppress the penetration of EM waves. Prior art EM head imaging systems use conventional imaging antennas fabricated on rigid dielectric printed circuit boards (PCBs) or based on ceramic-loaded waveguides. The adherence to rigid conventional PCB boards limits the ability to improve the performance and control the size, compatibility, flexibility, and portability of such systems.

In accordance with some embodiments of the present invention, there is provided a wearable antenna assembly for tomographic brain imaging of a subject, the antenna assembly including:
- a resilient cap to be worn on the head of a subject whose brain is to be imaged;
- an array of antennas at least partially embedded in the cap at respective mutually spaced locations such that, when the cap is worn by the subject, the antennas are arranged around the subject's brain;
- wherein the cap has a multi-layered structure including a layer composed of graphite and aluminium oxide powders dispersed in poly-di-methyl-siloxane (PDMS) to improve the matching of dielectric properties with those of the subject's head.

In some embodiments, the composition of the layer provides a relative permittivity of about 20 and a loss tangent of about 0.016 at 1 GHz.

In some embodiments, the graphite and aluminium oxide powders are dispersed in the PDMS in a ratio of about 0.2:1.8:10 by weight.

In some embodiments, the antennas are arranged in two rows around the subject's brain.

In some embodiments, the cap includes a layer of PDMS between the subject's head and the transceiving element of each antenna.

In some embodiments, the ground planes of the antennas are mutually spaced to allow flexibility and resilience of the cap.

In some embodiments, the transceiving element of each antenna is configured with multiple openings and multiple pins shorting the transceiving element to the corresponding ground plane such that the antenna supports multiple resonances and its output is substantially unidirectional and wideband when coupled to the subject's head.

In some embodiments, the cap includes two spaced halves formed of a first resilient material and joined by a second resilient material that is more stretchable than the first resilient material, so that the cap is wearable by subjects having a greater range of head sizes.

In some embodiments, each antenna is electrically connected to a common multi-pin connector by respective RF cables, the multi-pin connector being attached to the cap.

In some embodiments, each antenna includes an integral coaxial connector having a signal pin directly connected to the transceiving element of the antenna, and a grounding part directly connected to the ground plane of the antenna.

In accordance with some embodiments of the present invention, there is provided a method of forming a wearable antenna assembly for tomographic brain imaging of a subject, the method including the steps of:

forming a resilient cap to be worn on the head of a subject whose brain is to be imaged, including at least partially embedding an array of antennas in the cap at respective mutually spaced locations such that, when the cap is worn by the subject, the antennas are arranged around the subject's brain; wherein the resilient cap has a multi-layered structure including a layer of a matching material composed of graphite and aluminium oxide powders dispersed in PDMS to improve the matching of dielectric properties with those of the subject's head.

In accordance with some embodiments of the present invention, there is provided a method of forming a wearable antenna assembly for tomographic brain imaging of a subject, the method including the steps of:

forming a first layer of PDMS;

forming generally planar transceiving elements and respective generally planar ground planes;

arranging the transceiving elements on the PDMS layer at respective mutually spaced locations;

forming, over the transceiving elements and the first layer of PDMS, a layer of a matching material composed of graphite and aluminium oxide powders dispersed in PDMS to improve the matching of dielectric properties with those of the subject's head;

arranging the ground planes on the layer of matching material at respective mutually spaced locations aligned with the locations of the transceiving elements; and forming a second layer of PDMS over the ground planes and the layer of matching material to encapsulate the ground planes;

wherein the resulting assembly is in the form of a resilient cap to be worn by a subject whose brain is to be imaged, the transceiving elements and respective ground planes form respective antennas embedded within the cap.

In some embodiments, the method includes forming the matching material by mixing graphite and aluminium oxide powders with PDMS in jelly form and allowing it to harden.

In some embodiments, the composition of the matching material is graphite:aluminium oxide powder:PDMS in a ratio of about 0.2:1.8:10 by weight.

In some embodiments, the method includes connecting the antennas to a common multi-pin connector by respective RF cables, and attaching the multi-pin connector to the cap.

In accordance with some embodiments of the present invention, there is provided a method of determining the relative spatial locations and orientations of antennas of an array of antennas arranged around the head of a subject whose brain is to be imaged using electromagnetic signals transmitted by the antennas and scattered from the brain of the subject, the method including the steps of providing respective fiducial markers for the antennas; using a 3D imaging camera to automatically identify the fiducial markers, determine the spatial locations and orientations of the fiducial markers, and process those and data representing an outer surface of the subject's head to determine the orientations of the antennas relative to the subject's head and the distance of each antenna to the subject's head.

In accordance with some embodiments of the present invention, there is provided an antenna of an array of antennas to be arranged around a body part of a subject to be imaged using electromagnetic signals transmitted by the antennas and scattered from the body part, the antenna including a generally planar transceiving element and a corresponding generally planar ground plane aligned with the transceiving element, the transceiving element being configured with multiple openings and multiple pins shorting the transceiving element to the ground plane such that the antenna supports multiple resonances and its output is substantially unidirectional and wideband when coupled to the body part of the subject.

In accordance with some embodiments of the present invention, there is provided a method of using magnetic material to improve the matching, bandwidth and signal penetration inside the human head, in addition to reducing the antenna size and enabling using larger number of antennas for better image quality.

Also described herein is a wearable antenna assembly for tomographic brain imaging of a subject, the antenna assembly including:

a resilient cap to be worn on the head of a subject whose brain is to be imaged;

an array of antennas at least partially embedded in the cap at respective mutually spaced locations such that, when the cap is worn by the subject, the antennas are arranged around the subject's brain;

each of the antennas including a generally planar transceiving element and a corresponding generally planar ground plane aligned with the transceiving element, wherein a matching material having a relative permittivity of at least 10 is disposed between the transceiving element and the ground plane.

Also described herein is a method of forming a wearable antenna assembly for tomographic brain imaging of a subject, the method including the steps of:

forming a first layer of PDMS;

forming generally planar transceiving elements and respective generally planar ground planes;

arranging the transceiving elements on the PDMS layer at respective mutually spaced locations;

forming, over the transceiving elements and the first layer of PDMS, a layer of a matching material having a relative permittivity of at least 10;

arranging the ground planes on the layer of matching material at respective mutually spaced locations aligned with the locations of the transceiving elements; and forming a second layer of PDMS over the ground planes and the layer of matching material to encapsulate the ground planes;

wherein the resulting assembly is in the form of a resilient cap to be worn by a subject whose brain is to be imaged, the transceiving elements and respective ground planes form respective antennas embedded within the cap.

In order to address the difficulties of the prior art, the inventors have developed a wearable, wideband, and lightweight antenna assembly for EM head imaging and brain stroke detection, based on polymer composite materials technology. This improves the physical compatibility, portability, and performance of an EM imaging system. In work leading up to the invention, the inventors developed multi-layered custom-made flexible polymer composite substrate materials. The multi-layered composite substrate materials consist of poly-di-methyl-siloxane (PDMS) polymer, microscale graphite, iron oxide ($FeO \cdot Fe_2O_3$) aluminium oxide ($Al_2O_3$), powders. In the described embodiments, each antenna element is etched and embedded inside the flexible substrate layers. With the capability of significantly lowering the physical size and enhancing the performance of the imaging system, three aspects of the wearable antenna assembly are summarised as follows:

a) The development of flexible multi-layered polymer composite substrate materials for the imaging antennas and EM head imaging system platform: PDMS is used as one substrate material for the antennas and the platform. It has well-suited mechanical and electrical features, including high flexibility, durability, transparency, and low dielectric losses. Furthermore, PDMS has a high volume resistivity (about $2.9 \times 10^{14}$ Ω-cm), which helps to prevent the generation of parasitic currents in the substrate that would degrade antenna performance. Another of the substrate materials is a mixture of PDMS with microscale aluminium oxide and graphite powders that provide favourable dielectric properties, including high permittivity, stability and reasonable losses. These additive materials possess an excellent dispersion and dissolution characteristic with PDMS. The electrical properties of the developed structure tuned by the concentration ratio of the aluminium oxide and graphite with PDMS are characterized to obtain dielectric properties that meet the performance requirements of EM head imaging systems, including enhancing the antenna matching with human body tissues, and the size of the antennas. Furthermore, the described multi-layered structure is highly flexible and compatible with the human head, allowing the antenna assembly to be worn like a swimming hat.

In addition, the magnetite iron oxide ($FeO \cdot Fe_2O_3$) that has favourable magnetic properties, such as low loss, high stability and excellent dispersion and dissolution characteristic with many other materials, can also be composited with the PDMS, and $Al_2O_3$ as the second version of the developed substrate. Such magnetic-based substrate possess promising RF properties due to its permeability that is greater than 1. The magnetite iron oxide will be mixed together with the PDMS and $Al_2O_3$ in different ratios to obtain the optimal electromagnetic properties that help to match the antenna with the human head. It will improve the electromagnetic wave penetration inside the head, widen antenna's bandwidth and reduce its physical size.

b) Imaging antenna arrays: As described above, antennas are the key element of an EM imaging system, as the detection capability, image resolution, and accuracy of the system are mainly based on the performance of those antennas. The compactness and portability of the system depends on the size and weight of the imaging antenna array. The most important characteristics of each antenna element to achieve an efficient and compact EM head system are wideband, unidirectional, high front-to-back ratio (FTBR) EM performance, and low profile and compact mechanical properties. The wideband, unidirectional, and high FTBR features are required to ensure high penetration depth of EM waves into the human head tissues, which results in a high signal to noise ratio (SNR) that enhances the useful reflected signal from a stroke or other anomaly inside the brain. An array of imaging antennas that meets the abovementioned requirements is described herein, based on the developed tuneable flexible substrate and embedded inside a hat-like support structure having an elliptical shape around the head.

c) hardware architecture for a portable and wearable EM head imaging system: The described antenna assembly is based on a multi-layered flexible support structure or 'cap' that can be worn in the same manner as a swimming cap. Although the developed materials based on PDMS are highly flexible, their stretch-ability is limited. To fit the cap with different head shapes, two halves of the cap are formed from the flexible substrates and then interconnected by a thin stretchable and flexible silicone membrane. As a low-cost structure, the cap can be formed in different sizes to fit extremely different head sizes. An antenna array with optimized performance is embedded in the cap to achieve an efficient scanning inside the head. The antenna array is shielded by an array of conductive copper sheet acting as a ground plane for the antenna array. These conductive patches are separated by small gaps to ensure the flexibility of the cap, and to ensure that all layers of the structure are affixed together.

For successful image reconstruction, the exact location of each antenna around the head needs to be known to determine the corresponding time delay of the scattered signals that convey useful information. The exact locations and the geometrical arrangement of the imaging antennas are critically required for the imaging process algorithms. Since the antenna assembly is conformal to the head of the wearer, the inner-facing structure of the assembly and the antennas are directed inwards towards the head at different angles. This creates unequal distances and asymmetrical angles among the antenna elements in the array, and it is difficult to directly determine the exact location of each antenna. For different human heads, the antennas of the array will have different positions. To overcome these challenges, a 3D-depth camera technology can be used to determine the exact location of each antenna, specifically the excitation port of each imaging antenna. Then, this information is included in the image processing algorithm as a priori information.

When in use, the imaging antennas are connected to a large dynamic range VNA (or microwave transceiver) through RF coaxial cables. A calibration for the VNA and RF cables is performed to eliminate noise that might affect the accuracy of the results. Then, the VNA generates and transmits and receives the signals via the imaging antennas. The reflected signals from a stroke or other anomaly are collected by the VNA and simultaneously sent to the computer for signal processing and image reconstruction using proper processing algorithms, such as radar-based or tomographic techniques. The whole system is low-cost, portable and lightweight.

DESCRIPTION OF THE DRAWINGS

Some embodiments of the present invention are hereinafter described, by way of example, only, with reference to the accompanying drawings, wherein.

DETAILED DESCRIPTION

Figure 1:
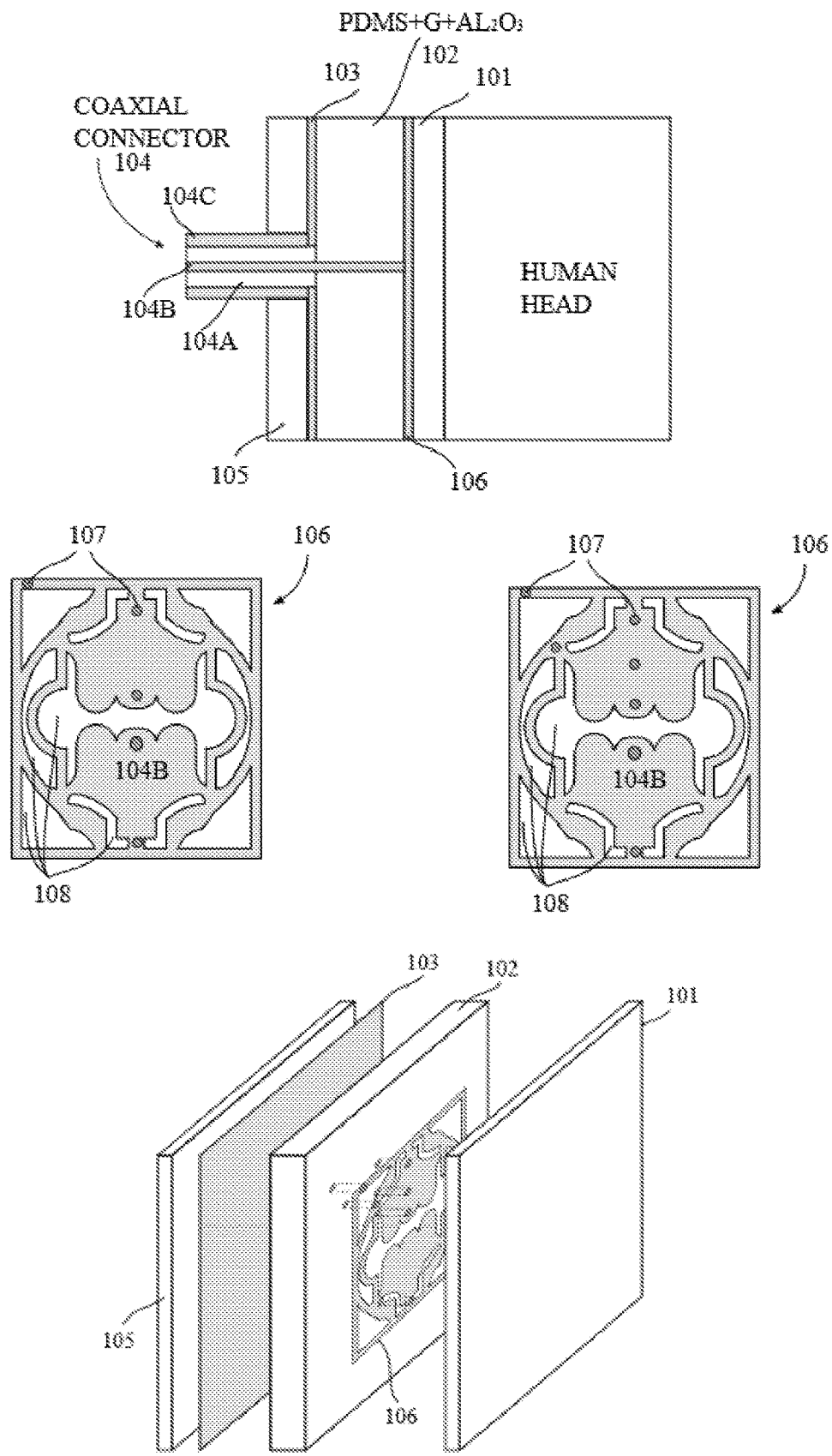
FIG. 1 includes a schematic cross-sectional side view of an antenna component of an antenna assembly in accordance with an embodiment of the present invention, plan views of an antenna structure of the antenna component (left-hand side) and of an alternative antenna structure of an alternative embodiment (right-hand side), and an exploded view illustrating the arrangement of layers of the antenna component.
Figure 3:
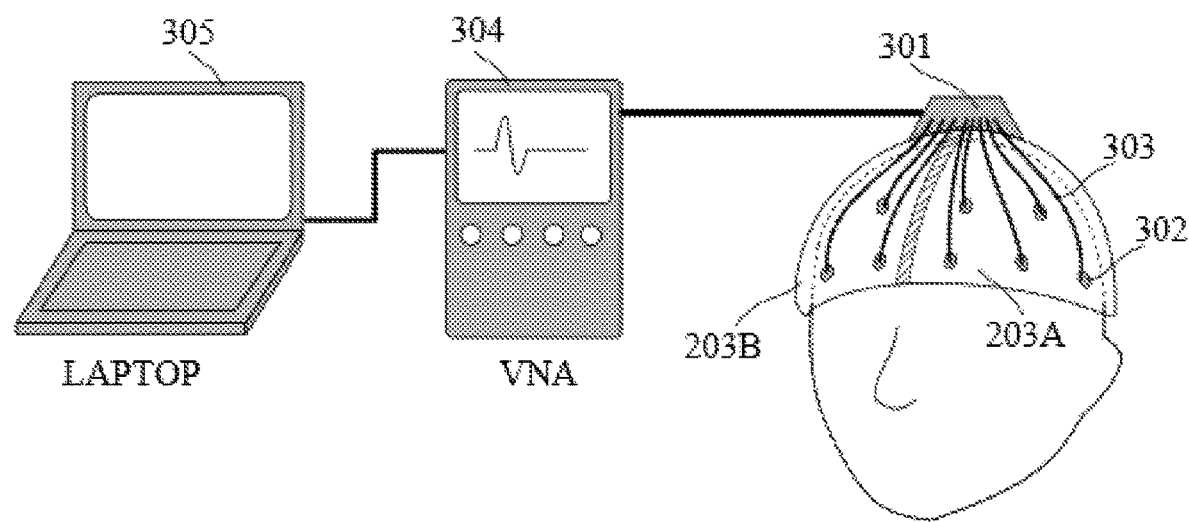
FIG. 3 is a schematic diagram of a system for brain tomography, including a wearable antenna assembly in accordance with an embodiment of the present invention.

As shown in FIG. 3, an electromagnetic medical imaging system for detecting brain injuries includes an antenna assembly 102, a vector network analyser (VNA) 204, and an analysis component 206. The antenna assembly 102 is wearable, and is shown in FIG. 1 being worn on the head of a human subject whose brain is to be imaged. The antenna assembly 102 includes an array of antennas disposed about the subject's head so that each antenna of the array can be selectively energised to radiate electromagnetic waves or signals of microwave frequency into the subject's brain to be scattered and the corresponding scattered signals detected by all of the antennas of the array, including the antenna that transmitted the corresponding signal. For convenience of reference, the overall process of sequentially causing each antenna of the array to transmit a corresponding microwave signal and using the antennas to receive the corresponding scattered signals is referred to herein as 'a scan'.

As known by those skilled in the art, the vector network analyser (VNA) 110 energises the antennas across the frequency band of 0.5 to 2 GHz as described above, and records the corresponding signals from the antennas as data (referred to herein as 'scattering' data) representing the amplitudes and phases of the scattered microwaves in a form that is known in the art as "scattering parameters" or "S-parameters". The VNA 110 sends this data to the analysis component 206 for processing to generate images of internal features of the subject's head (e.g., brain clots, bleeding sites, and other features) and to classify those features (e.g., as brain clots or bleeding sites).

In accordance with the described embodiments of the present invention, the antenna assembly includes an array of antennas embedded in a flexible and resilient composite material so that the assembly can be stretched over the head of a human subject and worn like a swimming cap. The antenna array is a compact, lightweight and portable array of wideband antennas, making it suitable for a portable electromagnetic medical imaging system.

A. Antenna Assembly

The antenna array is part of a wearable, wideband, compact and light-weight antenna assembly, as shown in FIG. 3, that improves the physical compatibility, portability, and performance of the system. The antenna assembly (FIG. 3) is in the general form of a flexible and elastically deformable and resilient wearable cap (similar to a swimming cap) in which the antenna array is embedded, allowing the antenna array to be aligned with and secured in close proximity to the subject's head. The cap is composed of a composite material, being a mixture of poly-di-methyl-siloxane (PDMS), microscale graphite (G), and aluminium oxide ($Al_2O_3$) powders selected to increase the relative permittivity of the composite material from the pure PDMS value of 2.9 to a value of greater than 10, thus improving the match to the dielectric properties of the human head, which typically has a relative permittivity of about 45. On the other hand, the magnetite iron oxide ($FeO \cdot Fe_2O_3$) can also be mixed with PDMS and $Al_2O_3$ to form the magnetic-based composite substrate. The magnetic-based substrate is developed to enhance the antenna match on the head, bandwidth, penetration, and reduce the antenna's physical size.

For convenience of reference, the first composite material is referred herein to as "PDMS-G-$Al_2O_3$" and the magnetic-based substrate material is PDMS-$FeO \cdot Fe_2O_3$—$Al_2O_3$. The first developed substrate is made as follows. First, the PDMS polymer elastomer consists of two components: a base resin and a curing agent. The base resin is mixed with the curing agent with a weight ratio of 10:1. Then micro-particles of graphite and aluminium oxide are dispersed in the PDMS elastomer with different ratios, as described below. The mixing solutions are stirred using a magnetic stirrer to ensure that the resulting structures are homogeneous. Then the mixtures are cured by placing them in an oven dryer at 55° C. for 3 to 4 hours in a hat mould. The hat mould which has the anatomic shape of human head is fabricated using a 3D printer. The dielectric properties of the composite PDMS-G-$Al_2O_3$ mixtures are then characterized and assessed using a dielectric probe kit and the Vector Network Analyser 110. Based on the results, optimal proportions of mixing ingredients can be determined and used for antenna optimization.

Specifically, the relative permittivity of pure PDMS is 2.9 with a loss tangent of 0.013 at 1 GHz. By mixing the PDMS, microscale graphite and aluminium oxide (PDMS-G-$Al_2O_3$) in a weight ratio of 10:0.2:1.8, respectively, the relative permittivity is increased to 20 with a loss tangent of 0.016 at 1 GHz. Since the average permittivity of a human head is approximately 45, this significantly improves the matching of the antenna to the human head, while limiting the dielectric loss of the antenna element. The PDMS-G-$Al_2O_3$ material is extremely flexible; for example, a full bending of 180° (U-shaped bend) is possible for sheet thicknesses up to at least 10 mm.

The magnetic-based substrate is formed from a composition of PDMS, microscale of iron oxide and aluminium oxide in a weight ratio of 10:2:2, respectively. The fabrication process of this substrate is as described above for the first substrate, except that the graphite is replaced by iron oxide.

B. Antenna Array

Figure 2:
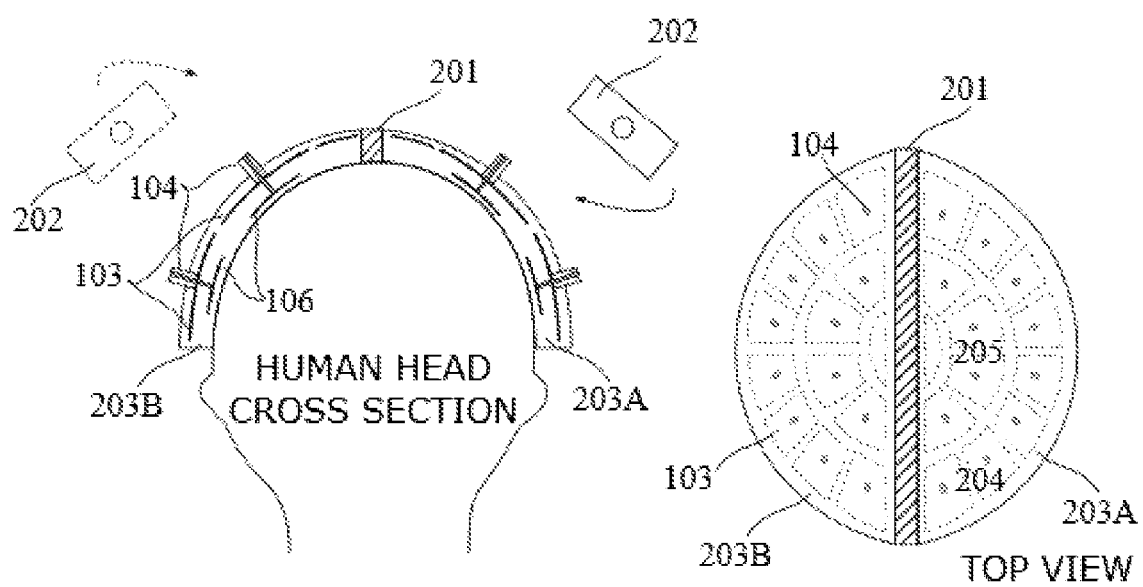
FIG. 2 includes a cross-sectional side view of the antenna assembly being worn by a subject whose brain is to be imaged, and a plan view of the antenna assembly.

As shown in FIGS. 1 and 2, each antenna of the antenna array includes a conductive copper sheet acting as an antenna ground plane 103, a conductive multi-slotted radiating element 106, and conductive pins 107 connecting the ground plane 103 to respective locations of the radiating element 106. In the described embodiment, the radiating element 106 includes four electrically conductive shorting pins 107 as shown in the left-hand column, centre row of FIG. 1. However, this need not be the case in other embodiments; for example, the right-hand column, centre row of FIG. 1 shows an alternative embodiment where the radiating element 106 includes six shorting pins 107.

Figure 7:
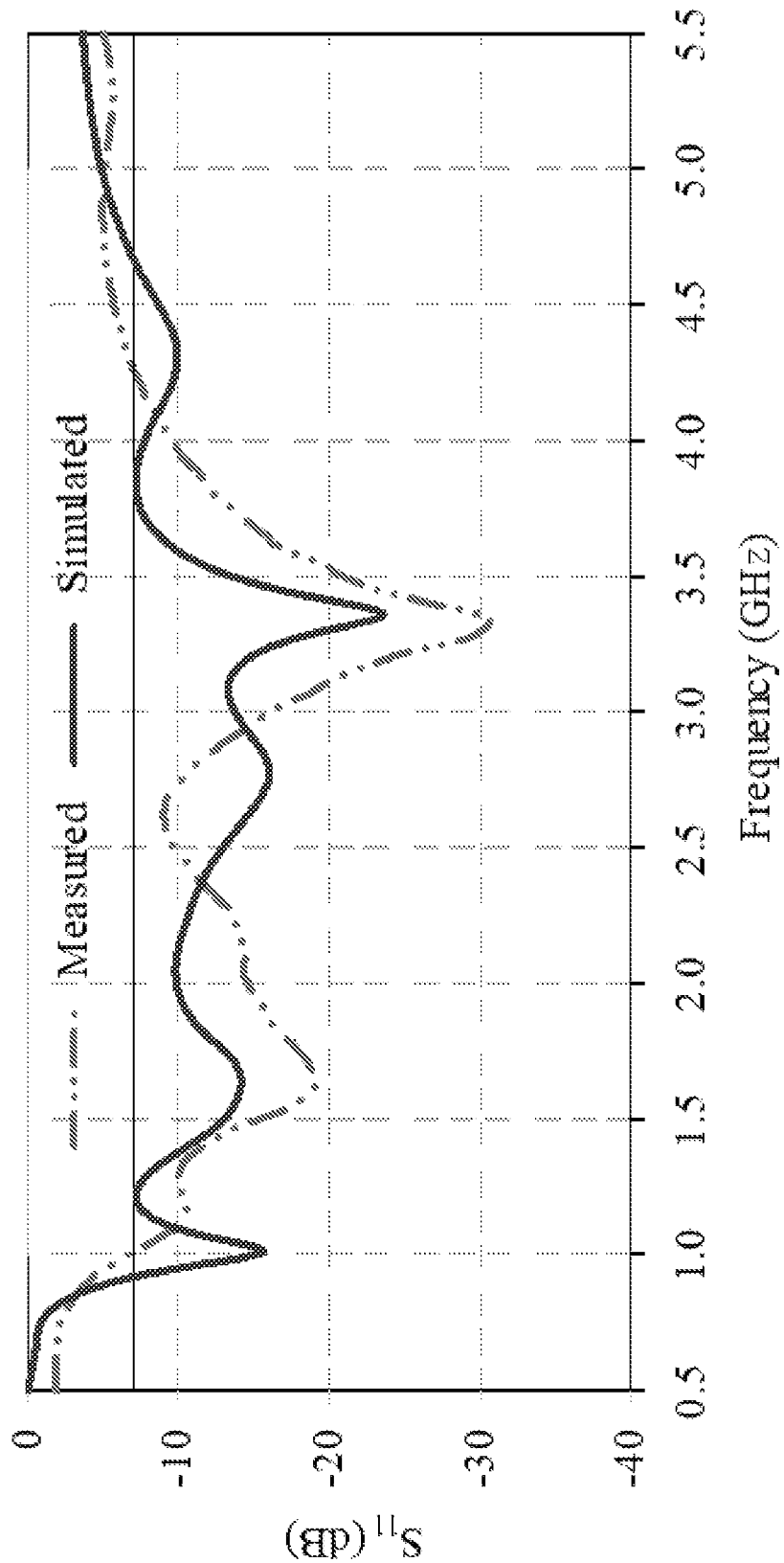
FIG. 7 is a graph of the simulated and measured reflection coefficients (S11) of the single antenna element.

As shown in the top part of FIG. 1, each antenna also includes a corresponding coaxial connector 104, including a hollow cylindrical Teflon insulating sleeve 104A surrounding an inner pin 104B connected to a corresponding location of the radiating element, and an outer case 104C connected to the ground plane 103. The conductive ground plane 103 and the radiating element 106 are attached to opposite surfaces of the flexible composite PDMS-G-$Al_2O_3$ layer 102, which acts as the antenna substrate. The high permittivity of the composite substrate material allows significant miniaturization of the antenna elements. Each antenna is configured as a modified multi-slotted planar magneto-electric (ME) dipole antenna. The electric dipoles are created by the two-side multi-slotted radiating patch 106, while the magneto dipoles are introduced by the parallel and sides shorted pins 107. The magneto and electric dipoles are jointly form a planar ME dipole. Such configuration allows further miniaturization and wideband performance due to the increase in the electrical length by the multi-slot 108 in the patch and the creation of multiple resonances by the shorting pins 107 of each radiating element. Simulated and measured reflection coefficients (S11) of the single element (with four shorting pins) 108 are shown in FIG. 7.

Two pure PDMS layers 101, 105 are attached to the exposed faces of the ground plane 103 and the radiating element 106, so that each antenna includes a stack of layers consisting of an outer PDMS layer 105, ground plane 103, composite PDMS-based material as either PDMS-G-Al2O3 or PDMS-Fe2O3-Al2O3 layer 102, radiating element 106, and inner PDMS layer 101. Due to its low-permittivity which could reduce signal penetration into the subject's head, the inner PMDS substrate layer 101 disposed between the radiating element 106 and the subject's head is relatively thin, being 1 mm in the described embodiments. By contrast, the thickness of the outer PDMS layer 105 above the ground plane 103 is not critical in terms of system performance, and is chosen to be 1 mm simply to reduce the weight of the wearable antenna assembly. The radiating elements 106 and ground planes 103 are embedded between the PDMS layers 101, 105, protecting the antenna array from dust, corrosion, water and rust, and allowing the antenna assembly to be robust in challenging environments.

In the described embodiments, the lateral dimensions of each antenna element are 2.5 cm×2.8 cm, with a thickness of 0.025 mm. As shown in FIG. 2, the antennas are arranged as two generally concentric elliptical rings 204, 205 around the subject's head. The lower and outer ring 204 includes 16 antennas, and the upper and inner ring 205 includes 8 antennas. The ground plane 103 acts as an electromagnetic shield for the system. In order to maintain the flexibility of the wearable antenna assembly, a full solid conductive ground plane is not used. Instead, finite copper sheets separated by small gaps are employed. This configuration ensures a lightweight, compact assembly, and in practice only an insignificant electromagnetic power leaks through the gaps between the ground plane sheets 103.

The wearable antenna assembly is configured as a stretchable and resilient cap to be worn by the subject. Although the PDMS and PDMS-G-Al$_2$O$_3$ materials are extremely flexible, they nevertheless have limited capability for stretching. Consequently, in order to allow the cap to fit different head sizes and shapes, in some embodiments the cap is formed as two halves 203A and 203B that are then interconnected by a thin and highly stretchable and flexible membrane 201, as shown in FIG. 2. The thickness of the outer PDMS layer 105, the ground plane 103, the composite PDMS-G-Al$_2$O$_3$ layer 102, the radiating element 106, the inner PDMS layer 101 and the cap interconnecting membrane 201 are 1 mm, 0.012 mm, 3.5 mm, 0.012 mm, 1 mm, and 3.5 mm, respectively. For extreme head sizes, caps of different sizes can be produced at low cost.

C. Fabrication Process

Figure 5:
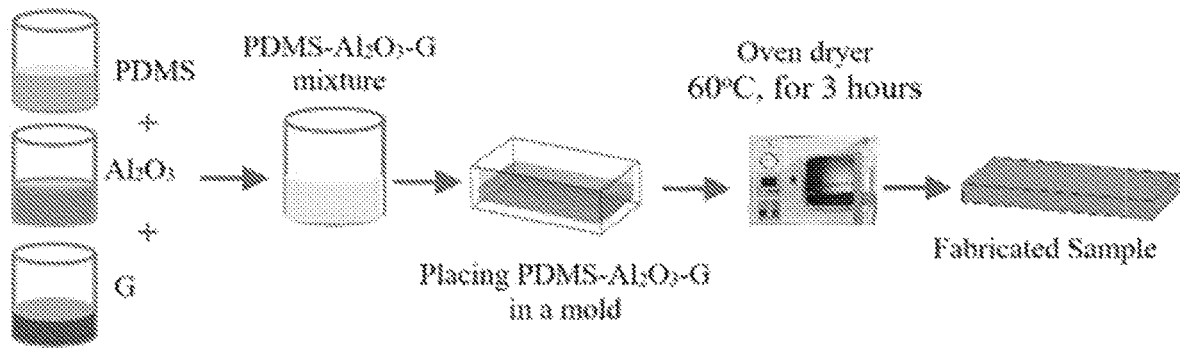
FIG. 5 is a schematic illustration of a fabrication process of the composite substrate.
Figure 6:
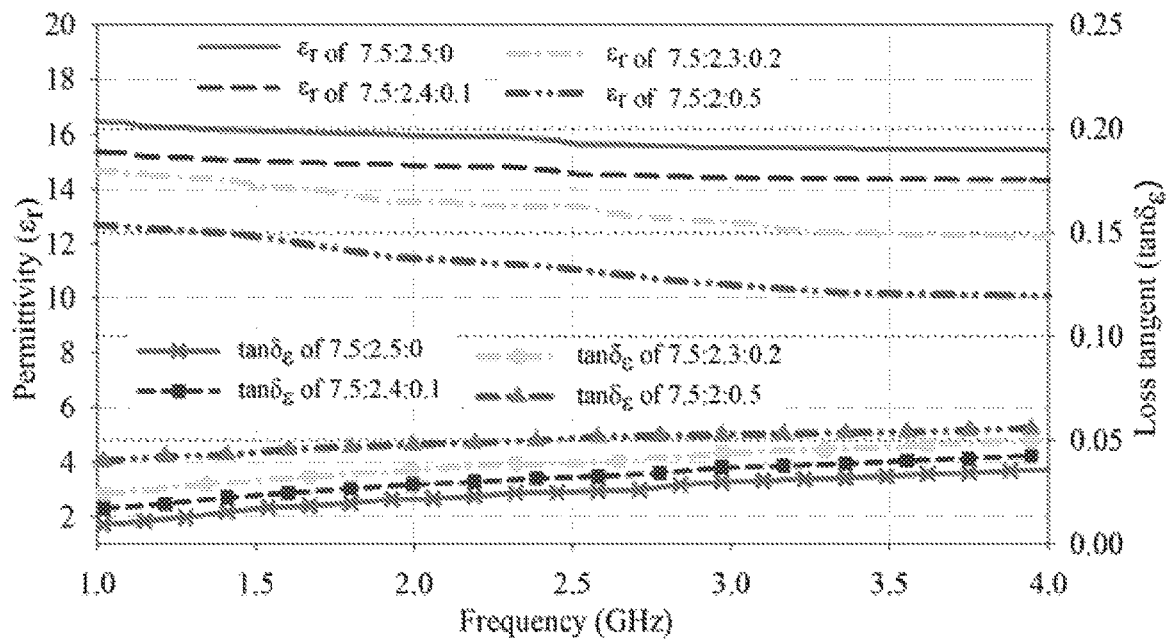
FIG. 6 is a graph of the measured values of dielectric properties (Permittivity, and loss tangent) of the composite substrate.

The fabrication process of the complete 3D multi-layered wearable assembly is summarized as follows, with reference to FIG. 5. First, the 1-mm inner PDMS layer 101 is produced. Once this layer has hardened, in a second step, the antenna elements 106 are formed (by stamping and etching 0.012 mm copper sheet and attached to one side of the inner PDMS layer 101 at respective locations in accordance with the general arrangement shown in FIG. 2. Then the composite PDMS-G-Al$_2$O$_3$ layer 102 of thickness 3.5 mm is produced and hardened on the radiating element 106 and attached to the inner PDMS layer 101. In the next step, 0.012-mm thick copper sheet is cut to form the ground planes 103 of the antennas and are attached to the composite PDMS-G-Al$_2$O$_3$ layer 102 at respective locations so that they are aligned with the respective antenna elements 106. Finally, a 1-mm PDMS layer is attached to form the outer PDMS layer 105 covering the ground planes 103. At the end, all the layers are bonded together to form one composite structure because the PDMS is highly adhesive when it is in jelly form. The dielectric properties of several PDMS-G-Al$_2$O$_3$ samples with different concentrations are shown in FIG. 6.

The layers are formed and assembled on a 3D hat mould with adjustable thickness. In the described embodiments, the mould is fabricated using 3D printer technology. The 3D mould is used to form the anatomic shape of the human head and to ensure there is no significant air gap between the wearable cap and the skin of the subject's head.

Each antenna element is associated with a corresponding RF connector 104. In the described embodiment, the RF connector 104 is a 50Ω coaxial connector that is used to excite the antenna, and is connected to a short length of high-quality RF cable 302 that is routed along the outer PDMS layer 105, as shown in FIG. 3, to a common multi-pin terminal 301 located on the top of the cap. In other embodiments, the cables can be replaced by low loss transmission lines that form part of the flexible substrate. Those lines can be integrated with a switching matrix on the flexible substrate, and thus only one RF cable and a control line are needed to connect the antenna assembly to the external transceiver and processing unit.

C. Antenna Array Location and 3D Depth Camera

For successful image reconstruction, the relative locations of the antennas arranged around the subject's head need to be known to determine the corresponding time delay of the scattered microwave signals. When the cap is worn by a subject, the antenna array becomes generally conformal with the subject's head, but the antennas can still have different orientations and distances relative to the subject's head. In view of this, a 3D camera and image processing can be used to determine the spatial location and orientation of each antenna, specifically the excitation port of each imaging antenna.

Figure 4:
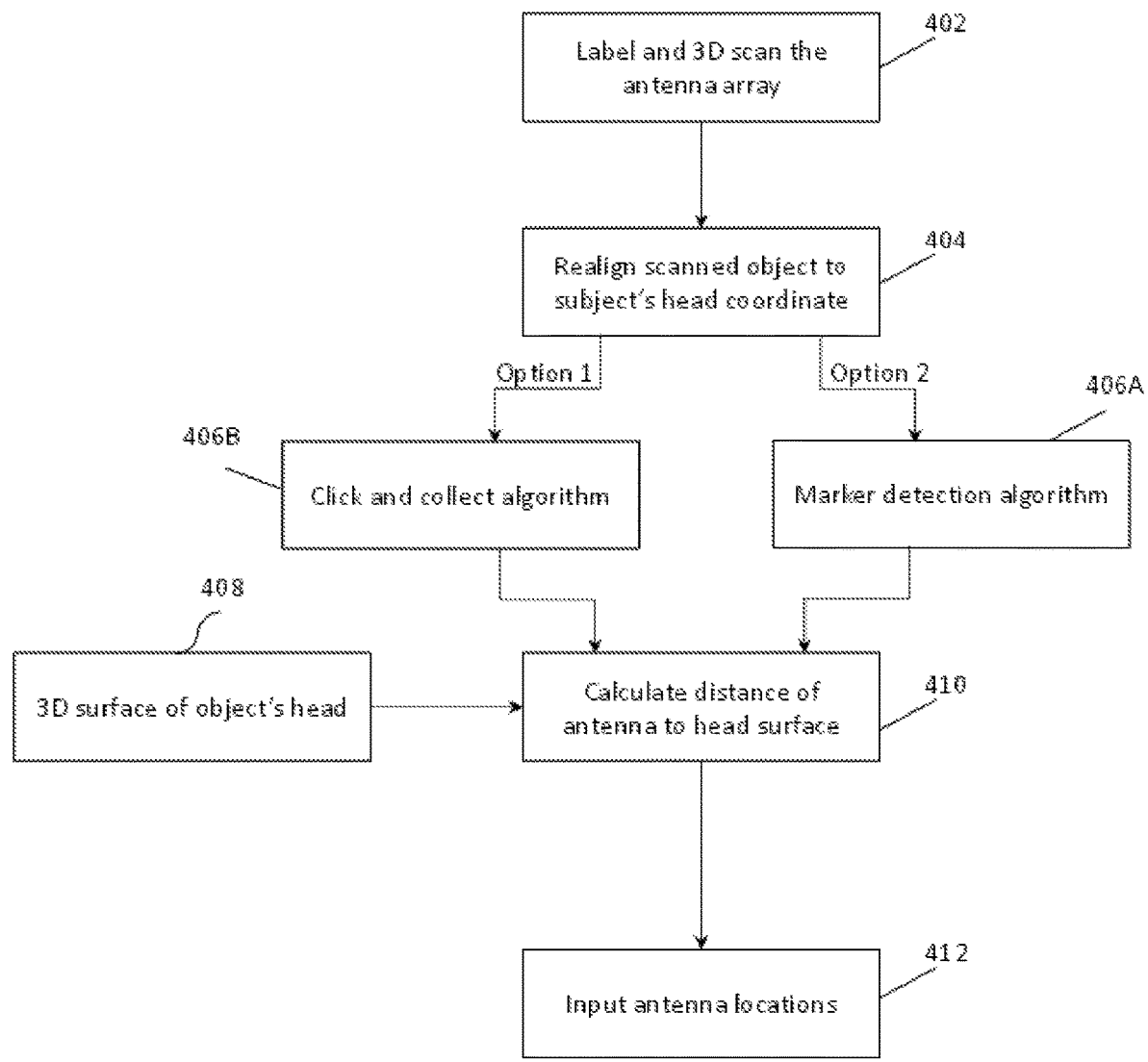
FIG. 4 is a flow diagram of a process for determining the spatial locations and orientations of the antennas relative to the subject's head.

A process for localising antenna locations begins at step 402, as shown in FIG. 4, by performing labelling and scanning the antenna array placed on the head surface. The scanning is to acquire a 3D structure of the antenna array, while different labels, which are each in form of an Aruco marker—a square marker consisting of a wide black border and an identifier in small square white shapes represented by an inner binary matrix—are attached; next the antenna ports 302, are used as anchor points for detecting the antenna locations. The scanned image contains the information of the spatial distribution of the array as well as the coded markers for each antenna. To ensure the antenna positions are represented in the same coordinate system with the imaging system, the scanned structure is aligned to a normalised coordinate system at step 404.

At step 406, the antenna locations are determined using information from the scanning process, i.e the aligned structure and the markers. In one embodiment, a click and collect method 406A is used. The aligned structure including the markers is imported and visually represented. The antennas' locations are manually determined by clicking on corresponding markers while its positions (antenna locations) are recorded and calculated accordingly by using the developed codes. In an alternative embodiment, a marker detection algorithm 406B is used. The system automatically identifies the position of each antenna by utilising the Open Source Computer Vision Library (Opencv). This process includes two main steps: detecting and classifying the marker candidates. In a first step, the scanned image is analysed to find square shapes (in black and white colors) which are the candidates for the markers. In a next step, the marker candidates are classified to confirm whether or not they are real markers by analysing their inner codification, which is represented by the white square shapes that contain a unique binary matrix of each marker. This involves extracting and analysing marker bits of each marker in which markers' images are thresholded and divided to determine and separate the black and white bits. The bits are then analysed to confirm whether the marker is known (e.g., whether it belongs to the system's marker library). Furthermore, this step also confirms which marker represents which antenna, based on unique codes of each marker. When the markers are confirmed, their spatial locations are stored and are used to determine the antennas' locations (by taking into account the known offset between each marker location and the location of its corresponding antenna).

At step 410, the system uses the detected antenna locations and the 3D head surface of subject's head 408 to calculate the relative distance between each of antenna to the head surface. Furthermore, by using the antenna location and subject's head surface, the orientation of each antenna towards the head surface are also determined.

Many modifications will be apparent to those skilled in the art without departing from the scope of the present invention.

The invention claimed is:

1. A wearable antenna assembly for tomographic brain imaging of a subject, the antenna assembly including:
   a resilient cap to be worn on the head of a subject whose brain is to be imaged;
   an array of antennas at least partially embedded in the cap at respective mutually spaced locations such that, when the cap is worn by the subject, the antennas are arranged around the subject's brain;
   wherein the cap has a multi-layered structure including a layer composed of graphite and aluminium oxide powders dispersed in poly-di-methyl-siloxane (PDMS) to improve the matching of dielectric properties with those of the subject's head.

2. The antenna assembly of claim 1, wherein the composition of the layer provides a relative permittivity of about 20 and a loss tangent of about 0.016 at 1 GHz.

3. The antenna assembly of claim 1, wherein the graphite and aluminium oxide powders are dispersed in the PDMS in a ratio of about 0.2:1.8:10 by weight.

4. The antenna assembly of claim 1, wherein the antennas are arranged in two rows around the subject's brain.

5. The antenna assembly of claim 1, wherein the cap includes a layer of PDMS between the subject's head and the transceiving element of each antenna.

6. The antenna assembly of claim 1, wherein the ground planes of the antennas are mutually spaced to allow flexibility and resilience of the cap.

7. The antenna assembly of claim 1, wherein the transceiving element of each antenna is configured with multiple openings and multiple pins shorting the transceiving element to the corresponding ground plane such that the antenna supports multiple resonances and its output is substantially unidirectional and wideband when coupled to the subject's head.

8. The antenna assembly of claim 1, wherein the cap includes two spaced halves formed of a first resilient material and joined by a second resilient material that is more stretchable than the first resilient material, so that the cap is wearable by subjects having a greater range of head sizes.

9. The antenna assembly of claim 1, wherein each antenna is electrically connected to a common multi-pin connector by respective RF cables, the multi-pin connector being attached to the cap.

10. The antenna assembly of claim 1, wherein each antenna includes an integral coaxial connector having a signal pin directly connected to the transceiving element of the antenna, and a grounding part directly connected to the ground plane of the antenna.

11. A method of determining the relative spatial locations and orientations of antennas of an array of antennas arranged around the head of a subject whose brain is to be imaged using electromagnetic signals transmitted by the antennas and scattered from the brain of the subject, the method including the steps of providing the wearable antenna assembly of claim 1; providing respective fiducial markers for the antennas; using a 3D imaging camera to automatically identify the fiducial markers, determine the spatial locations and orientations of the fiducial markers, and process those and data representing an outer surface of the subject's head to determine the orientations of the antennas relative to the subject's head and the distance of each antenna to the subject's head.

12. A method of forming a wearable antenna assembly for tomographic brain imaging of a subject, the method including the steps of:
   forming a resilient cap to be worn on the head of a subject whose brain is to be imaged, including at least partially embedding an array of antennas in the cap at respective mutually spaced locations such that, when the cap is worn by the subject, the antennas are arranged around the subject's brain; wherein the resilient cap has a multi-layered structure including a layer of a matching material composed of graphite and aluminium oxide powders dispersed in PDMS to improve the matching of dielectric properties with those of the subject's head.

13. A method of forming a wearable antenna assembly for tomographic brain imaging of a subject, the method including the steps of:
   forming a first layer of PDMS;
   forming generally planar transceiving elements and respective generally planar ground planes;
   arranging the transceiving elements on the PDMS layer at respective mutually spaced locations;
   forming, over the transceiving elements and the first layer of PDMS, a layer of a matching material composed of graphite and aluminium oxide powders dispersed in PDMS to improve the matching of dielectric properties with those of the subject's head;
   arranging the ground planes on the layer of matching material at respective mutually spaced locations aligned with the locations of the transceiving elements; and
   forming a second layer of PDMS over the ground planes and the layer of matching material to encapsulate the ground planes;
   wherein the resulting assembly is in the form of a resilient cap to be worn by a subject whose brain is to be imaged, the transceiving elements and respective ground planes form respective antennas embedded within the cap.

14. The method of claim 13, including forming the matching material by mixing graphite and aluminium oxide powders with PDMS in jelly form and allowing it to harden.

15. The method of claim 14, wherein the composition of the matching material is graphite:aluminium oxide powder: PDMS in a ratio of about 0.2:1.8:10 by weight.

16. The method of claim 13, including connecting the antennas to a common multi-pin connector by respective RF cables, and attaching the multi-pin connector to the cap.

\* \* \* \* \*